United States Patent [19]

Herbst et al.

[11] Patent Number: 5,961,790
[45] Date of Patent: Oct. 5, 1999

[54] SEPARATION OF (METH) ACRYLIC ACID BY RECTIFICATION

[75] Inventors: Holger Herbst, Frankenthal; Gerhard Nestler, Ludwigshafen, both of Germany; Jerry Darlington, Lake Jackson, Tex.; Ulrich Hammon, Mannheim, Germany

[73] Assignee: BASF Aktiengesellschaft, Ludwigshafen, Germany

[21] Appl. No.: 08/355,892

[22] Filed: Dec. 14, 1994

[51] Int. Cl.$^6$ .............................. B01D 3/34; C07C 51/44
[52] U.S. Cl. ..................................... 203/59; 203/DIG. 21; 562/600
[58] Field of Search ................... 203/59, 8, 42, 203/91, 38, DIG. 8, DIG. 21; 562/600

[56] References Cited

U.S. PATENT DOCUMENTS

| | | | |
|---|---|---|---|
| 3,725,208 | 4/1973 | Maezawa et al. | 203/8 |
| 3,893,895 | 7/1975 | Dehnert et al. | 203/38 |
| 4,828,652 | 5/1989 | Schrapp | 562/600 |
| 5,196,578 | 3/1993 | Kuragano et al. | 562/531 |
| 5,426,221 | 6/1995 | Willersinn | 562/600 |
| 5,482,597 | 1/1996 | Herbst et al. | 562/600 |

FOREIGN PATENT DOCUMENTS

| | | |
|---|---|---|
| 0 270 999 | 6/1988 | European Pat. Off. . |
| 0 312 191 | 4/1989 | European Pat. Off. . |
| 0 685 448 | 12/1995 | European Pat. Off. . |
| 2 136 396 | 2/1973 | Germany . |
| 2 207 184 | 8/1973 | Germany . |
| 22 07 184 | 8/1973 | Germany . |
| 2 235 326 | 2/1974 | Germany . |
| 43 08 087 | 9/1994 | Germany . |
| 4 436 243 | 4/1996 | Germany . |
| 0252446 | 12/1985 | Japan . |
| 1 346 737 | 2/1974 | United Kingdom . |

*Primary Examiner*—Virginia Manoharan
*Attorney, Agent, or Firm*—Oblon, Spivak, McClelland, Maier & Neustadt, P.C.

[57] ABSTRACT

A process for the separation by rectification of (meth)acrylic acid from a mixture containing (meth)acrylic acid and an inert hydrophobic organic liquid having a boiling point higher than that of (meth)acrylic acid as main constituents and also lower aldehydes as secondary constituents, a primary amine and/or a salt thereof are added.

2 Claims, No Drawings

SEPARATION OF (METH) ACRYLIC ACID BY RECTIFICATION

BACKGROUND OF THE INVENTION

1. Field of the Invention

The present invention relates to a novel process for the separation by rectification of (meth)acrylic acid from a mixture containing (meth)acrylic acid and an inert hydrophobic organic liquid having a boiling point higher than that of (meth)acrylic acid as main constituents and also lower aldehydes as secondary constituents.

2. Discussion of the Background (Meth)acrylic acid is used as an abbreviation and denotes acrylic acid or methacrylic acid.

(Meth)acrylic acid, either as such or in the form of its esters, is particularly important for preparing polymers for a very wide range of applications, eg., use as adhesives.

(Meth)acrylic acid can be obtained, inter alia, by catalytic gas-phase oxidation of alkanes, alkanols, alkenes or alkenals containing 3 or 4 carbon atoms. It can be particularly advantageously obtained, for example, by catalytic gas-phase oxidation of propene, acrolein, tert-butanol, iso-butene, iso-butane, iso-butyraldehyde or methacrolein. However, other possible starting compounds are those from which the actual $C_3/C_4$ starting compound is only formed as an intermediate during the gas-phase oxidation. An example which may be mentioned is the methyl ether of tert-butanol.

These starting gases, generally diluted with inert gases such as nitrogen, CO, $CO_2$, saturated hydrocarbons and/or steam, are passed in admixture with oxygen at elevated temperatures (usually from 200 to 400° C.) and, if desired, superatmospheric pressure over transition metal mixed oxide catalysts (eg. containing Mo, V, W and/or Fe) and converted by oxidation into (meth)acrylic acid (cf., for example, DE-A 4 405 059, EP-A 253 409, EP-A 92 097, DE-A 44 31 957 and DE-A 44 31 949).

However, owing to the numerous parallel and subsequent reactions occurring in the course of the catalytic gas-phase oxidation, and also because of the inert diluent gases used, the product is not pure (meth)acrylic acid but rather a reaction mixture which contains essentially (meth)acrylic acid, the inert diluent gases and byproducts, from which the (meth)acrylic acid has to be separated. Besides byproducts which are comparatively simple to remove from (meth) acrylic acid and cause relatively little interference in subsequent use of the (meth)acrylic acid, such as acetic acid, the reaction mixture also contains, in particular, lower aldehydes which are closely related to (meth)acrylic acid and are therefore difficult to separate from (meth)acrylic acid, such as formaldehyde, acetaldehyde, acrolein, methacrolein, propionaldehyde, n-butyraldehyde, benzaldehyde, furfural and crotonaldehyde and possibly also maleic anhydride (based on the amount of (meth)acrylic acid present in the reaction gas mixture, the total amount of these secondary components which frequently cause considerable interference in subsequent use is generally <2% by weight).

DE-A 44 36 243 relates to a process for separating (meth)acrylic acid from the reaction gas mixture of the catalytic gas-phase oxidation by countercurrent absorption using a high-boiling inert hydrophobic organic liquid, in which the reaction gas mixture is passed through an absorption column in countercurrent to the descending high-boiling inert hydrophobic organic liquid, a rectification process is superimposed on the absorption process occurring naturally in the absorption column, by withdrawing from the absorption column an amount of energy greater than its natural energy loss resulting from its contact with the surroundings, and the (meth)acrylic acid is separated by rectification from the liquid discharge from the absorption column (absorbate), which contains (meth)acrylic acid and the absorbant as main constituents and lower aldehydes and, possibly, maleic anhydride as secondary constituents. The (meth)acrylic acid obtainable in this way is described as crude (meth)acrylic acid. It generally has a purity >98% by weight, with the impurities coming, in particular, from among the specified lower aldehydes and possibly maleic anhydride, while the separation of the (meth)acrylic acid from the high-boiling inert organic absorption liquid is essentially quantitative.

DE-A 44 36 243 defines high-boiling inert hydrophobic organic liquids (absorbants) as all those liquids whose boiling point at atmospheric pressure is above the boiling point of (meth)acrylic acid and which comprise at least 70% by weight of those molecules which contain no outward-acting polar group and are thus, for example, not able to form hydrogen bonds. This definition also applies here.

DE-C 2 136 396 and DE-A 43 08 087 likewise disclose the separation of acrylic acid from the reaction gas mixture of the catalytic gas-phase oxidation of propylene and/or acrolein by countercurrent absorption using a high-boiling inert hydrophobic organic liquid. The process is carried out essentially by passing the reaction gas mixture through a conventional absorption column in countercurrent to the descending absorption liquid, then, in a desorption column, largely removing the easily separable, readily volatile secondary components from the liquid discharge of the absorption column, composed of acrylic acid, the absorbant and secondary components, by stripping with inert gas, and subsequently treating by rectification the liquid discharge of the desorption column, which contains (meth)acrylic acid and the absorbant as main constituents and lower aldehydes and possibly maleic anhydride as secondary constituents, to separate off crude acrylic acid.

However, a disadvantage of the separation by rectification of crude (meth)acrylic acid from mixtures containing (meth) acrylic acid and a high-boiling inert hydrophobic organic liquid as main constituents and lower aldehydes and possibly maleic anhydride as secondary constituents is that during the course of rectification, despite use of amounts which are customary per se of customary polymerization inhibitors such as phenothiazine, paramethoxyphenol, paranitrosophenol, hydroquinone, hydroquinone monomethyl ether or air, the rectification apparatus (in particular the vaporizer surface and the internal fixtures of the column) become covered with a deposit. If the separation by rectification is operated continuously, the different coloration of the deposit in the stripping column (black) and the rectifying column (white) demonstrates that at least two processes participate in deposit formation. The formation of this deposit is disadvantageous because it has to be removed from time to time, which requires a shutting down of the rectification operation.

It is an object of the present invention to provide a process for the separation by rectification of (meth)acrylic acid from a mixture containing (meth)acrylic acid and an inert hydrophobic organic liquid having a boiling point higher than that of (meth)acrylic acid as main constituents and lower aldehydes as secondary constituents, which process makes possible reduced deposit formation and thereby extended rectification operation.

SUMMARY OF THE INVENTION

We have found that this object is achieved by the separation by rectification of (meth)acrylic acid from a mixture containing (meth)acrylic acid and an inert hydrophobic organic liquid having a boiling point higher than that of (meth)acrylic acid as main constituents and lower aldehydes as secondary constituents, which comprises carrying out the rectification with addition of a primary amine and/or salts thereof. For the purposes of the present invention, a primary amine is a compound containing at least one —NH$_2$ group.

The following prior art was able to be used as a starting point.

DE-B 22 07 184 and GB-B 1 346 737 disclose a process for purifying crude acrylic acid wherein at least one primary amine such as, for example, hydrazine, phenylhydrazine, aniline, monoethanolamine, ethylenediamine and/or glycine is added to the crude acrylic acid and the acrylic acid is separated from the mixture by distillation.

The primary amines added here obviously bind to the aldehydes, which are present as impurities, to a high degree, so that even a subsequent simple distillative separation step achieves a high separation performance in respect of the aldehydic impurities. EP-A 270 999 similarly recommends the addition of guanylhydrazine (aminoguanidine) and/or salts thereof (preferably aminoguanidine hydrogen carbonate) to the crude (meth)acrylic acid prior to the distillative workup and U.S. application Ser. No. 08/347,131, U.S. Pat. No. 5,482,597, (O.Z. 0050/45375, NAE 642/94) discloses a process for purifying a crude (meth) acrylic acid contaminated with lower aldehydes, in which the (meth)acrylic acid is admixed with a carboxylic acid hydrazide and/or salts thereof and the (meth)acrylic acid is separated from the mixture by distillation.

However, a disadvantage of these proposals of the prior art for removing the lower aldehydes from crude (meth) acrylic acid is that the presence of the primary amines during the distillative workup of the crude (meth)acrylic acid causes increased deposit formation on the surfaces of the distillation apparatus (cf., for example DE-A 43 35 172 and U.S. application Ser. No. 08/347,131, U.S. Pat. No. 5,482,597, (O.Z. 0050/45375, NAE 642/94). Attempts are made to counter this deposit formation by additionally adding an organic sulfonic acid.

Obviously, direct reaction products of the primary amine added with the aldehydic impurities and/or subsequent products formed from these during the distillative workup take part in the increased deposit formation.

It has now surprisingly been found that in the process of the invention, which differs from the treatment by distillation (rectification) of a crude (meth)acrylic acid by, in particular, the presence of a high-boiling inert hydrophobic organic liquid, not only does the increase in deposit formation to be expected from the presence of the primary amine not occur, but the deposit formation observed is even reduced in comparison with distillation carried out in the absence of the primary amine. At the same time, the process of the invention gives a crude (meth)acrylic acid whose content of lower aldehydes and maleic anhydride is substantially decreased.

Examples which may be mentioned of primary amines and/or salts thereof which can be added according to the invention are (in the interests of simplicity, only the amine form is listed; the salts are those corresponding to these amines): hydrazine and its derivatives such as guanylhydrazine (aminoquanidine) and phenylhydrazine, aromatic amines which preferably have up to 12 carbon atoms, such as aniline, o-, m-, p-toluidine and o-, m-, p-nitroaniline, aminocarboxylic acids such as glycine, aminoalcohols such as ethanolamine (2-aminoethanol), or else linear, branched or cyclic aliphatic amines having from 1 to 12 carbon atoms, such as methylamine. Of course, polyvalent primary amines are also possible, ie. suitable compounds include those which have more than one, for example 2, 3 or 4, —NH$_2$ groups. Examples which may be mentioned are 1,2-diaminoethane, putrescine (tetramethylenediamine) and cadaverine (pentamethylenediamine).

Suitable salts of the primary amines to be added are, in particular, their hydrogen carbonates, nitrates, sulfates or chlorides. Examples which may be mentioned are aminoguanidinium hydrogen carbonate, which is the preferred aninoguanidine compound.

A group of primary amines which is particularly advantageous according to the invention is that comprising the hydrazides of organic carboxylic acids. Suitable hydrazides of organic carboxylic acids are, in particular: semicarbazide (carbamic acid hydrazide) and the monohydrazides and dihydrazides of saturated aliphatic monocarboxylic and/or dicarboxylic acids having from 1 to 10 carbon atoms. These are, in particular, the hydrazides of formic acid, acetic acid, propionic acid, butanoic acid and pentanoic acid. Suitable saturated aliphatic dicarboxylic acids for the corresponding hydrazides are, in particular, those which have from 4 to 8 carbon atoms. The dihydrazides of adipic acid and succinic acid acid are particularly suitable. Of course, it is also possible to use salts of the carboxylic acid hydrazides in place of the hydrazides themselves. Suitable salts are, for example, their hydrogen carbonates, nitrates, sulfates or chlorides, for example semicarbazide hydrochloride.

The amount of the primary amine to be added according to the invention is selected according to, in particular, the aldehyde content of the liquid mixture from which the (meth)acrylic acid is to be separated by rectification. This can be determined in a manner known to those skilled in the art, after appropriate derivatization of the aldehyde, by the method of high-pressure liquid chromatography (HPLC). Generally at least 0.5 mol, but normally not more than 5 mol, of primary amine is added per mol of aldehydic impurities The amount of primary amine to be added is, on the same basis, preferably from 1 to 3 mol and particularly preferably from 1 to 2 mol.

The process of the invention is of particular importance in the case of methacrylic acid which is prepared by gas-phase catalytic oxidation of methacrolein, in particular when the methacrolein is produced by gas-phase catalytic oxidation of tert-butanol, iso-butane or iso-butene or by reaction of formaldehyde with propionaldehyde as described in EP-B 92 097 or EP-B 58 927, and this particularly when the gas-phase catalytic oxidation of the tert-butanol, iso-butane or iso-butene is carried out using a catalytically active composition of the general formula I $$MO_{12}Bi_aFe_bX^1{}_cX^2{}_dX^3{}_eX^4{}_gO_n \qquad (I),$$

in which the variables have the following meanings:

X$^1$—nickel and/or cobalt,

X$^2$—thallium, an alkali metal and/or an alkaline earth metal,

X$_3$—phosphorus, arsenic, boron, antimony, tin, cerium, lead, niobium and/or tungsten, X$^4$—silicon, aluminum, titanium and/or zirconium, a—from 0.5 to 5, b—from 0.01 to 3, c—from 3 to 10, d—from 0.02 to 2, e—from 0 to 5, g—from 0 to 10 and n—an integer which is determined by the valence and amount of the elements other than oxygen in I, at from 300 to 400° C. and, apart from the specific temperature-time profile, otherwise under the conditions described in DE-A 40 23 239 and the methacrolein obtained is used for further oxidation without intermediate purification. Furthermore, the process of the invention is particularly useful when the gas-phase catalytic oxidation of the methacrolein, apart from the specific temperature-time profile, is carried out as described in DE-A 41 32 263 at from 200 to 350° C. or as described in DE-A 41 32 684 at from 250 to 400°C.

Furthermore, the process of the invention is particularly suitable in the case of acrylic acid which has been prepared by gas-phase oxidation in one step starting from acrolein or in two steps starting from propylene via acrolein. This applies particularly when the catalytic gas-phase oxidation of the propylene is carried out using a multi-metal oxide catalyst of the general formula II

$$MO_{12}Bi_aFe_bX^1_cX^2_dX^3_eX^4_gO_n \qquad (II),$$

in which the variables have the following meanings:

X¹—nickel and/or cobalt,

X²—thallium, an alkali metal and/or an alkaline earth metal,

X₃—phosphorus, arsenic, boron, antimony, tin, cerium, lead and/ or tungsten,

X⁴—silicon, aluminum, titanium and/or zirconium, a—from 0.5 to 5, b—from 0.01 to 3, c—from 3 to 10, d—from 0.02 to 2, e—from 0 to 5, g—from 0 to 10 and n—an integer which is determined by the valence and frequency of the elements other than oxygen, and the catalytic gas-phase oxidation of the acrolein is carried out using a multi-metal oxide catalyst of the general formula III

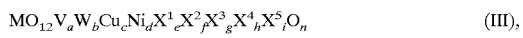

$$MO_{12}V_aW_bCu_cNi_dX^1_eX^2_fX^3_gX^4_hX^5_iO_n \qquad (III),$$

in which the variables have the following meanings:

X¹—one or more alkali metals,

X²—one or more alkaline earth metals,

X₃—chromium, manganese, cerium and/or niobium,

X⁴—antimony and/or bismuth,

X⁵—silicon, aluminum, titanium and/or zirconium, a—from 1 to 6, b—from 0.2 to 4, c—from 0.5 to 6, d—from 0.2 to 6, e—from 0 to 2, f—from 0 to 3, g—from 0 to 5, h—from 0 to 40, i—from 0 to 40 and n—an integer which is determined by the valence and amount of the elements other than oxygen.

The reaction gases of the first oxidation step are usually fed to the second oxidation step without intermediate purification.

The reaction conditions usually used can be taken from, for example, DE-A 44 31 957 and DE-A 44 31 949.

The process of the invention is particularly useful when the mixture containing (meth)acrylic acid and an inert hydrophobic organic liquid having a boiling point higher than that of (meth)acrylic acid as main constituents and lower aldehydes as secondary constituents has been obtained from the reaction gas mixtures of the abovementioned gas-phase oxidations as liquid discharge from a countercurrent absorption process with subsequent desorption by stripping using an inert gas as described in DE-C 21 36 396 or DE-A 43 08 087 or as liquid discharge from a countercurrent absorption process with superimposed rectification as described in DE-A 43 36 243.

High-boiling inert hydrophobic organic absorption liquids which can be used are, in particular, all those which are recommended in DE-A 21 36 396 and DE-A 43 08 087. These are essentially liquids whose boiling point at atmospheric pressure is above 160° C. Examples which may be mentioned are middle oil fractions from paraffin distillation, diphenyl ether, biphenyl, or mixtures of the abovementioned liquids such as, for example, a mixture of from 70 to 75% by weight of diphenyl ether and from 25 to 30% by weight of biphenyl. The use of a mixture comprising a mixture of from 70 to 75% by weight of diphenyl ether and from 25 to 30% by weight of biphenyl is favourable. Particularly favorable is the use of a mixture comprising a mixture of from 70 to 75% by weight of diphenyl ether and from 25 to 30% by weight of biphenyl, and, based on this mixture, from 0.1 to 25% by weight of dimethyl phthalate.

Frequently, the high-boiling inert hydrophobic organic liquid in the absorption column is used in such amounts that the liquid discharge contains from 5 to 25, usually from 5 to 15, % by weight of (meth)acrylic acid.

The separation by rectification according to the invention of (meth)acrylic acid is preferably carried out under reduced pressure, advantageously at a pressure of <100 mbar at the top of the column, generally from 10 to 100 mbar. Correspondingly, the liquid-phase temperatures are from 100 to 2220° C., however, it can also be carried out at pressures of up to 1 bar.

Advantageously, the separation by rectification according to the invention of (meth)acrylic acid is carried out continuously, with the (meth)acrylic acid being drawn off via the top or a side outlet of the rectification column. The primary amine to be added according to the invention is here advantageously fed into the rectification column just below the discharge point for the (meth)acrylic acid. Notably, the process method of the invention effects a reduction in the deposit formation both in the rectification section and in the stripping section of the rectification column.

Suitable rectification columns are all the customary types, ie. the rectification column can be, for example, a bubble-tray or packed column. A bubble-tray column is preferably used. Advantageously, the point of the continuous feed of the liquid mixture from which the (meth)acrylic acid is to be separated by rectification is located, viewed starting out from the lowest theoretical plate, at about the end of the first third of the distance between the lowest and the highest theoretical plate.

The bottoms obtained from the separation by rectification of the invention can, in a continuous embodiment, be taken off continuously and, for example, reused directly as absorption liquid in the upstream absorption step. To increase the operating times of the plant, it is sometimes advisable to bleed off a substream of this high-boiling organic liquid and to recycle it only after separating off the absorbant in a workup step. Even better, the entire bottoms are subjected to such a workup step prior to being recycled to the absorption column. Of course, the primary amine to be added according to the invention can be added to the absorption column effecting the separation of the (meth)acrylic acid from the reaction gas mixture of the catalytic gas-phase oxidation or be added to any downstream desorption column so that direct addition to the-rectification column is partially or completely omitted. As already mentioned, the process of the invention is carried out in the presence of customary amounts of customary polymerization inhibitors, preferably phenothiazine. These are usually used in amounts of from 50 to 1000 ppm based on the amount of (meth)acrylic acid (weight).

The process of the invention gives a crude (meth)acrylic acid which is particularly low in lower aldehydic impurities. The operating time possible in continuous operation is significantly increased.

EXAMPLE

This was carried out in the presence of 200 ppm (based on the weight of acrylic acid) of phenothiazine as polymerization inhibitor.

Catalytic gas-phase oxidation of acrolein as described in Example B1 of DE-A 43 02 991 was used to produce a reaction gas mixture containing acrylic acid. 2.1 standard m$^3$/l of this reaction gas mixture were cooled to 170° C. in a gas cooler by injection of a coolant mixture comprising 57.4% by weight of diphenyl ether, 20.7% by weight of biphenyl and 20% by weight of dimethyl phthalate. In a separator, the portion of the coolant which has remained liquid was then separated from the gas phase comprising reaction gas and vaporized coolant. The gas phase, which had a temperature of 170° C., was introduced below the first tray into a bubble-tray column containing 27 trays having a diameter of 80 mm and exposed to the countercurrent of 3 l/h of the absorbant like-wise comprising 57.4% by weight of diphenyl ether, 20.7% by weight of biphenyl and 20% by weight of dimethyl phthalate which was introduced at a temperature of 45° C. at the top of the column. The discharge from the absorption column was indirectly heated to 105° C. in a heat exchanger and passed to the top of a desorption column which was configured as a bubble-tray column having 20 trays. In the desorption column, low-boiling components such as acetic acid which are easily separated off in comparison with acrylic acid were largely removed from the mixture otherwise containing acrylic acid/lower aldehydes/absorbant by means of stripping with nitrogen (400 l/h, countercurrent). The discharge from the desorption column was fed, at the level of the tenth tray, into a rectification column comprising 35 bubble trays (diameter of the column: 80 mm) and the acrylic acid was continuously taken off under reduced pressure at the level of the twenty-sixth bubble tray in a purity of 98.5% by weight. The temperature at the bottom of the rectification column was 160° C. The pressure at the top was 80 mbar, that at the bottom was 100 mbar.

Comparison was made between the possible operating times of the rectification column in the absence and in the presence of adipic acid dihydrazide. When adipic acid dihydrazide (ADH) was used, this was added to the rectification column directly below the outlet point of the crude acrylic acid in such an amount that an ADH content of 400 ppm (based on the total weight) was present in the rectification section.

Result:

a) Stripping section: without ADH, the maximum operating time was 100 h; after that shut-down was necessary for removal of the deposit; with ADH, an operating time of 230 h was achieved;

b) Rectification section: without ADH the maximum operating time was 50 h; after that shut-down was necessary for removal of the deposit; with ADH, an operating time >230 h was achieved.

The content of lower aldehydes in the crude acrylic acid separated off by rectification was, at 400 ppm (based on the weight of the crude acrylic acid), less than one third of the content of lower aldehydes, based on acrylic acid, of the liquid mixture fed to the rectification column.

If the ADH was all added to the desorption column, the operating time in the stripping section was increased by 100% compared with direct complete ADH addition to the rectification column.

We claim:

1. A process for the separation of (meth)acrylic acid from a mixture comprising the step of:

rectifying a mixture comprising (meth)acrylic acid, an inert hydrophobic organic liquid having a boiling point higher than that of (meth)acrylic acid, comprising diphenyl ether and/or a mixture thereof, and lower aldehydes, in the presence of a primary amine and/or a salt thereof, wherein (meth)acrylic acid is separated from said inert hydrophobic liquid and said lower aldehydes; and wherein rectification is performed in a rectification column and said primary amine and/or salt thereof is not added directly to said rectification column.

2. A process for the separation of (meth)acrylic acid from a mixture comprising the step of:

rectifying a mixture comprising (meth)acrylic acid, an inert hydrophobic organic liquid having a boiling point higher than that of (meth)acrylic acid, comprising diphenyl ether and/or a mixture thereof, and lower aldehydes, in the presence of a primary amine and/or a salt thereof, which is carried out continuously and in which the amine is added to the rectification column directly below the outlet point for the (meth)acrylic acid; and wherein (meth)acrylic acid is separated from said inert hydrophobic liquid and said lower aldehydes.

* * * * *